Figure 1:
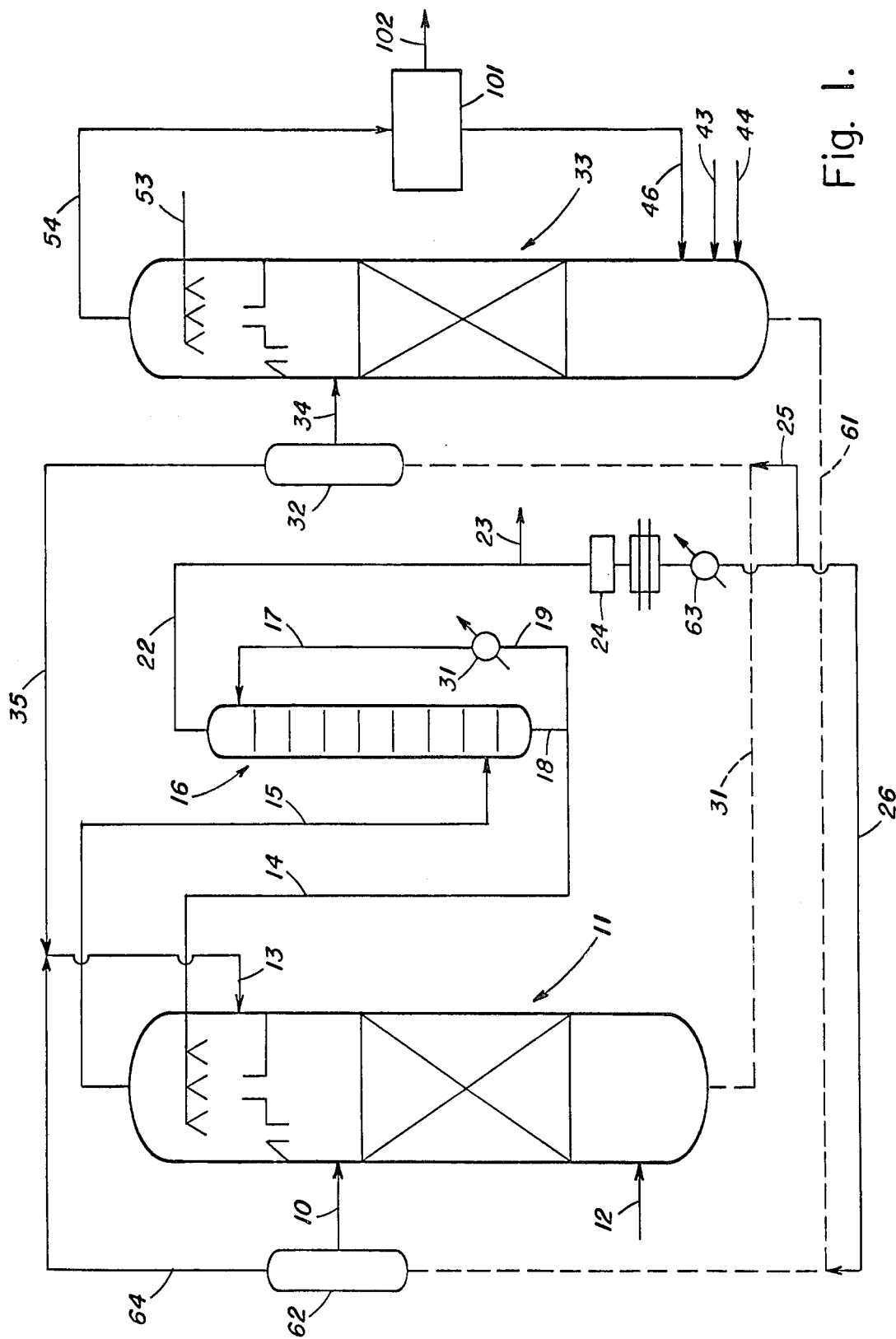

United States Patent [19]
Sze et al.

[11] 4,107,222
[45] Aug. 15, 1978

[54] OXYCHLORINATION OF METHANE

[75] Inventors: Morgan C. Sze, Upper Montclair; Herbert Riegel, Maplewood; Harvey D. Schindler, Paterson, all of N.J.

[73] Assignee: The Lummus Company, Bloomfield, N.J.

[21] Appl. No.: 631,157

[22] Filed: Nov. 11, 1975

Related U.S. Application Data

[63] Continuation of Ser. No. 299,848, Oct. 24, 1972, abandoned.

[51] Int. Cl.² ............................................ C07C 17/00
[52] U.S. Cl. .............................. 260/659 A; 260/659 R; 260/658 R
[58] Field of Search ........... 260/658 R, 659 A, 659 R, 260/652 P

[56] References Cited
U.S. PATENT DOCUMENTS

| | | | |
|---|---|---|---|
| 2,447,323 | 8/1948 | Fontana | 260/664 |
| 2,498,552 | 2/1950 | Kilgren et al. | 260/662 |
| 2,792,435 | 5/1957 | Lukes et al. | 260/662 |
| 3,126,419 | 3/1964 | Burks et al. | 260/662 |
| 3,548,016 | 12/1970 | Sze | 260/659 R |
| 3,848,007 | 11/1974 | Forlano | 260/658 R |
| 3,879,481 | 4/1975 | Sze et al. | 260/659 R |

FOREIGN PATENT DOCUMENTS

| | | | |
|---|---|---|---|
| 711,287 | 6/1965 | Canada | 260/659 A |
| 1,002,088 | 8/1965 | United Kingdom | 423/500 |

*Primary Examiner*—Delbert E. Gantz
*Assistant Examiner*—Joseph A. Boska
*Attorney, Agent, or Firm*—Marn & Jangarathis

[57] ABSTRACT

Methane is oxychlorinated to one or more chlorinated methanes, without net production of carbon tetrachloride, by contacting methane and chlorine and/or hydrogen chloride with a molten mixture of cuprous chloride, cupric chloride, and copper oxychloride, in the presence of an amount of carbon tetrachloride which inhibits its net production thereof.

7 Claims, 2 Drawing Figures

OXYCHLORINATION OF METHANE

This is a continuation, of application Ser. No. 299,848, filed Oct. 24, 1972, now abandoned.

This invention relates to chlorination and more particularly to a new and improved process for producing chlorinated methanes.

Commercial processes for producing chlorinated methanes generally involve the direct chlorination of methane. There is also available in the art a process for oxychlorinating methane to chlorinated methanes, but such an oxychlorination reaction generally has a low methane selectivity as the result of a high production of carbon oxides and/or dimers. In addition, the oxychlorination of methane is generally accompanied by the production of unwanted chlorinated methane byproducts as a result of the inherent production of all four chlorinated methane derivatives. Thus, for example, carbon tetrachloride, as a result of market conditions, in many cases, is not a desirable product.

Accordingly, there is a need in the art for a process for oxychlorinating methanes in a manner which maximizes methane selectivity to chlorinated methanes (minimizes production of carbon oxides and dimers), and minimizes production of carbon tetrachloride.

An object of the present invention is to provide a new and improved process for producing chlorinated methanes.

Another object of the present invention is to provide a new and improved process for oxychlorinating methane to produce chlorinated methanes.

A further object of the present invention is to provide a process for oxychlorinating methane while minimizing production of carbon tetrachloride.

Yet another object of the present invention is to oxychlorinate methane while minimizing production of carbon oxides.

Figure 2:
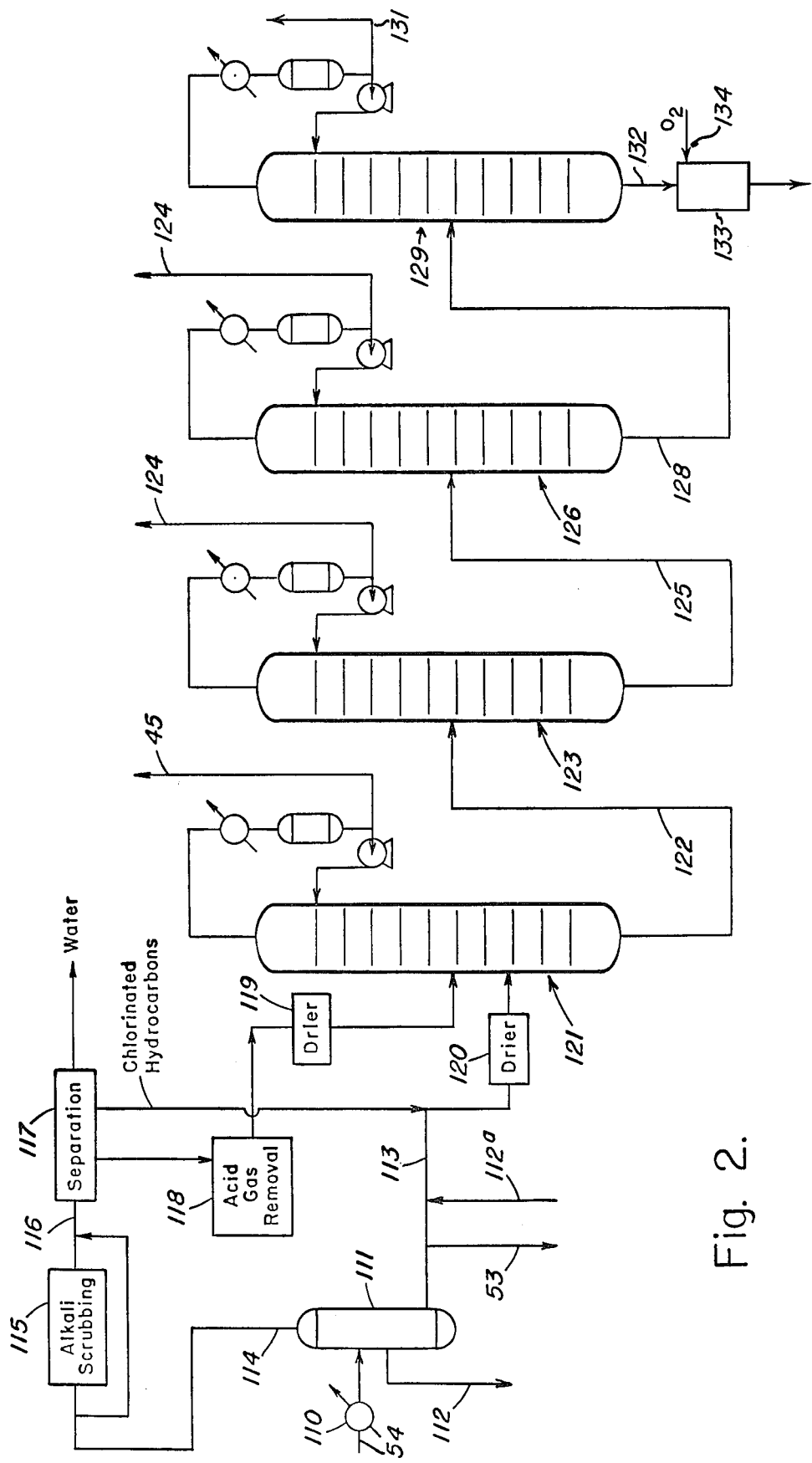

These and other objects of the present invention will become more apparent from reading the following description of the present invention with reference to the drawings wherein:

FIG. 1 is a simplified schematic flow diagram of an embodiment of the present invention; and FIG. 2 is a simplified schematic flow diagram of an embodiment for recovering chlorinated methane product.

The objects of the present invention are broadly accomplished by contacting methane and a chlorinating agent which is either chlorine and/or hydrogen chloride with a molten mixture containing cuprous chloride, cupric chloride and copper oxychloride in the presence of carbon tetrachloride, with the carbon tetrachloride being present in an amount which essentially eliminates net production thereof.

The copper chlorides are generally maintained in molten form by use of a metal salt melting point depressant which is non-volatile and resistant to the action of oxygen at the process conditions, such as a chloride of a univalent metal, i.e., a metal having only one positive valence state. The univalent metal chlorides, are preferably alkali metal chlorides, such as potassium and lithium chloride in particular, but it is to be understood that other metal chlorides and mixtures thereof, such as the heavy metal chlorides, i.e., heavier than copper, of Groups I, II, III, and IV of the Periodic Table; e.g., zinc, silver, and thallium chloride, may also be employed. The metal chloride melting point depressant is added in an amount sufficient to maintain the salt mixture as a melt at the reaction temperatures, and is generally added in an amount sufficient to adjust the melting point of the molten salt mixture to a temperature of below about 600° F. In the case of a salt mixture of copper chlorides and potassium chloride, the composition of the melt ranges between about 20% and about 40%, preferably about 30%, by weight, potassium chloride, with the remainder being copper chlorides. It is to be understood, however, that in some cases the catalyst melt may have a melting point higher than 600° F., provided the catalyst remains in the form of the melt throughout the processing steps. It is further to be understood that the melt may contain other reaction promoters.

The reaction sequence for producing chlorinated methanes, using methyl chloride, as a representative example is believed to be represented by the following equations:

(1) $2 CuCl_2 \rightarrow 2 CuCl + Cl_2$
(2) $CH_4 + Cl_2 \rightarrow CH_3Cl + HCl$
(3) $Cu O \cdot CuCl_2 + 2HCl \rightarrow 2CuCl_2 + H_2O$ The copper oxychloride is provided by contacting the molten mixture in a separate reaction zone with molecular oxygen, with the reaction being reprsented by the following equation:

(4) $2 CuCl + \frac{1}{2} O_2 \rightarrow Cu O \cdot CuCl_2$

The overall reactions for producing chlorinated methanes are represented by the following equations:

(5) $2 CH_4 + Cl_2 + \frac{1}{2} O_2 \rightarrow 2CH_3Cl + H_2O$
(6) $CH_4 + HCl + \frac{1}{2} O_2 \rightarrow CH_3Cl + H_2O$
(7) $CH_4 + Cl_2 + \frac{1}{2} O_2 \rightarrow CH_2Cl_2 + H_2O$
(8) $CH_4 + 2HCl + O_2 \rightarrow CH_2Cl_2 + 2 H_2O$
(9) $2CH_4 + 3Cl_2 + 3/2 O_2 \rightarrow 2CHCl_3 + 3H_2O$
(10) $CH_4 + 3HCl + 3/2 O_2 \rightarrow CHCl_3 + 3 H_2O$
(11) $CH_4 + 2Cl_2 + O_2 \rightarrow CCl_4 + 2 H_2O$
(12) $CH_4 + 4HCl + 2 O_2 \rightarrow CCl_4 + 4 H_2O$ In accordance with the present invention, carbon tetrachloride is present during the oxychlorination in an amount which eliminates net production thereof and such an amount will vary depending on the per pass methane conversion, and the chlorinated methanes recovered as net chlorinated methane product, (net chlorinated methane product is the chlorinated methane product which is not recycled to the oxychlorination reaction), and whether chlorine or hydrogen chloride is used as the chlorinating agent, with the required amount of carbon tetrachloride (the amount is calculated as mols of carbon tetrachloride to total mols of methane) increasing as either:methane conversion increases; hydrogen chloride is used instead of chlorine; or also as the content of more fully chlorinated methanes in the net chlorinated methane product increases. Thus, for example, in the case where chloroform is the only net chlorinated methane product, as hereinafter described, and per pass total methane conversion is at a value from about 25 mol.% to about 50 mol.% using only chlorine as the chlorinating agent, the amount of carbon tetrachloride required to essentially eliminate net production thereof, expressed as mols of carbon tetrachloride to mols of total methane, is from about 0.4:1 to about 0.7:1, respectively. An increase in the methane conversion will require an increase in the carbon tetrachloride to methane mol ratio and decrease in the methane conversion will result in a decrease in the carbon tetrachloride to methane mol ratio. In the case where hydrogen chloride is used as the sole chlorinating agent, for a range of methane conversion from about 15 mol% to about 25 mol%, the mol ratio of carbon tetrachloride to methane will vary from about 0.4:1 to about 0.6:1. Similarly, in the case where methylene chloride and chloroform are recovered as net reaction product, at a specified conversion, the mol ratio of carbon tetrachloride to total methane required to essentially eliminate net production of carbon tetrachloride will be less than that which is required, at the specified conversion, in the case where only chloroform is recovered as net reaction product. It should also be apparent that as methane conversion is decreased, the carbon tetrachloride to methane mol ratio required to essentially eliminate net production thereof is also decreased. In general, in the case where methylene chloride and chloroform are the only net reaction product, and chlorine is used as the chlorinating agent, at a methane conversion from about 25 mol% to about 50 mol%, the mol ratio of carbon tetrachloride to methane will vary from about 0.2:1 to about 0.3:1, with the higher mol ratios corresponding to higher methane conversions and higher amounts of chloroform in the net product. It is also to be understood that carbon tetrachloride may be added in amounts greater than that required to inhibit net production thereof.

In some cases, it may be desirable to recover only chloroform or only chloroform and methylene chloride as net reaction product. In such a case, methylene chloride and methyl chloride or only methyl chloride, respectively, are added to the oxychlorination in an amount which essentially eliminates net production thereof. As in the case of carbon tetrachloride, the particular amount which is added is dependent upon methane conversion, with the selection of the particular amount being within the scope of those skilled in the art from the teachings herein. In the case where only chloroform is recovered as net product, and per pass total methane conversion is from about 25 mol % to about 50 mol %, using only chlorine, the methyl chloride to methane mol ratio will generally vary from about 0.1:1 to about 0.5:1, respectively and the methylene chloride to methane mol ratio will vary from about 0.2:1 to about 0.6:1, respectively. If hydrogen chloride is used as the sole chlorinating agent, at a methane conversion from about 15 mol% to about 25 mol%, the methyl chloride to methane mol ratio would vary from about 0.2:1 to about 0.4:1 and the methylene chloride to methane mol ratio would vary from about 0.3:1 to about 0.5:1.

In accordance with the present invention, the effluent withdrawn from the oxychlorination reaction zone always includes the four chlorinated methane derivatives, including carbon tetrachloride. This, for example, in the case where net production of carbon tetrachloride is essentially eliminated the feed to the oxychlorination reaction zone includes carbon tetrachloride and, accordingly, the effluent from the oxychlorination reaction zone should include a corresponding amount of carbon tetrachloride. There is essentially no net production of carbon tetrachloride, however, in that the effluent does not include an amount of carbon tetrachloride which is greater than the amount of carbon tetrachloride introduced with the feed. The above is also applicable to the cases in which there is no net production of methyl chloride and/or methylene chloride. It is to be understood, however, that, for example, the process of the present invention also includes the recovery of methylene chloride and/or methyl chloride, as net product, with the methyl chloride and/or methylene chloride also being introduced into the oxychlorination reaction. In such a case, the methyl chloride and/or methylene chloride is insufficient to eliminate net production thereof, and is added to the oxychlorination reaction to increase the amount of more fully chlorinated derivatives (other than carbon tetrachloride) in the net product.

The oxychlorination reaction may be effected at temperatures from about 700° to about 950° F. It has been found, however, that the oxychlorination reaction temperature has a significant effect on per pass methane selectivity to chlorinated methanes. Thus, for example, methane selectivity to chlorinated methanes is disproportionally decreased (increased production of carbon oxide) by raising the oxychlorination reaction temperature from a temperature of 840° to a temperature of 870° F. Accordingly, in order to increase methane selectivity to chlorinated methanes, the oxychlorination is preferably effected at a temperature from about 700° to about 860° F., and more preferably at a temperature from about 800° to about 850° F. In accordance with the present invention, per pass methane selectivity to chlorinated methanes in the order of 75–90 mol % have been achieved. The pressure and residence time for the oxychlorination reaction may vary over a wide range, and in general, the pressure is from about 1 atm to about 10 atm and the residence time is from about 1 second to about 60 seconds.

The ratio of chlorine and/or hydrogen chloride to total methane (fresh feed and recycle) present in the oxychlorination reaction zone is determinative of methane conversion. Accordingly, based on total methane present and the chlorinated methane recycle, the amount of chlorine and/or hydrogen chloride which should be added to the oxychlorination reaction zone to provide the desired per pass methane conversion may be easily determined by those skilled in the art.

The molten mixture which is introduced into the oxychlorination reaction zone generally contains from about 20% to about 55%, by weight, of cupric chloride, and from about 0.5%, by weight, up to the oxychloride solubility in the melt, which is generally about 4%, by weight. The oxychloride is generally present in an amount from about 1% to about 3%, by weight. The oxychloride provides the oxygen requirements for the process and, accordingly, sufficient oxychloride must be present in the melt to meet such requirements. It is to be understood, however, that by adjusting the salt circulation rates, the amounts of the various components of the melt may be changed while still providing process requirements.

The oxychloride is generated by contacting the molten mixture in a separate reaction zone with molecular oxygen, generally air is used to provide the molecular oxygen, at a temperature from about 700° to about 950° F., and preferably from about 800° to about 900° F. The pressure is generally from about 1 atm to about 10 atm, and the residence time from about 1 to about 60 seconds. It is to be understood, however, that shorter or longer residence times may be used.

The invention will now be further described with reference to an embodiment thereof illustrated in the accompanying drawing. It is to be understood, however, that the scope of the invention is not to be limited thereby. It is further to be understood that the molten copper chloride salts are highly corrosive and, accordingly, the processing equipment must be suitable protected; e.g., the reactors may be lined with ceramic. Similarly, if pumps are used to transport the molten salts they must also be protected. The molten salts, however, are preferably transferred between the reactors by the use of gas lifts, as known in the art.

Referring now to FIG. 1, a molten chloride salt, such as a mixture of potassium chloride, cuprous chloride and cupric chloride in line 10, is introduced into the top of the reaction portion of an oxidation vessel 11 maintained as hereinabove described, at temperatures and pressures suitable for oxidizing the molten salt. A compressed oxygen-containing gas, such as air, in line 12, is introduced into the bottom of vessel 11 and is passed in countercurrent contact to the descending molten salt, resulting in oxidation of the salt to produce copper oxychloride with the concurrent evolution of heat.

An effluent gas, comprised essentially of the nitrogen introduced with the air, rises into the top of vessel 11 wherein the effluent gas is combined with lift gas, as hereinafter described, introduced through line 13. The effluent gas is directly contacted in the top of vessel 11 with a spray of quench liquid, in particular aqueous hydrogen chloride, introduced through line 14 to cool the effluent gas and thereby eliminate any vaporized and entrained salts therefrom. The effluent gas, now containing vaporized quench liquid, is withdrawn from vessel 11 through line 15 and introduced into a direct contact quench tower 16, of a type known in the art wherein the effluent gas is cooled by direct contact with a suitable quench liquid, in particular, aqueous hydrogen chloride introduced through line 17 to thereby remove vaporized quench liquid from the effluent gas.

The quench liquid is withdrawn from the bottom of tower 16 through line 18 and a first portion passed through line 14 for quenching the effluent gas in vessel 11. A second portion of the quench liquid is passed through line 19, containing a cooler 21 for introduction into the quench tower 16 through line 17.

An effluent gas, comprised essentially of nitrogen, is withdrawn from quench tower 16 through line 22 and a portion thereof purged through line 23. The remaining portion of the nitrogen effluent gas is compressed in compressor 24 and the temperature thereof regulated in heat exchanger 63 prior to passage through lines 25 and 26 for use as a lift gas for transporting molten salt, as hereinafter described.

The molten salt, now containing copper oxychloride, is withdrawn from the bottom of vessel 11 through line 31 and lifted by the lift gas in line 25 into a separation vessel 32 positioned adjacent the top of the reaction portion of a reaction vessel 33. In separator 32, the molten salt is separated from the lift gas, with the separated lift gas being withdrawn through line 35 and combined with lift gas from the oxidation reactor for introduction into the quenching portion of vessel 11 through line 13.

Fresh feed methane in line 44, fresh feed chlorine and/or hydrogen chloride, in line 43 and recycle methane and chlorinated methane(s), in line 45 are introduced into the bottom of reaction vessel 33 and contacted therein by the descending molten salt to effect chlorination of the methane to the desired chlorinated methane product. The chlorinated methane recycle includes carbon tetrachloride in an amount sufficient to essentially eliminate net production thereof; i.e., the amount of carbon tetrachloride withdrawn from reactor 33 is about equal to the amount introduced into reactor 33. Depending on the desired net product, the chlorinated methane recycle may include methyl chloride and may also include methylene chloride. As hereinafter described with reference to FIG. 2, methyl chloride is introduced in an amount to eliminate net production thereof, and methylene chloride, although introduced into reactor 33, is not introduced in an amount to eliminate net production thereof.

A reaction effluent, including chlorinated methanes (the reaction effluent includes methyl chloride, methylene chloride, chloroform and carbon tetrachloride) unconverted methanes, water vapor, some hydrogen chloride (generally corresponding to equilibrium amounts of hydrogen chloride) and carbon oxides, is directly contacted with a quench liquid, such as heavier chlorinated methanes, introduced through line 53 to cool the effluent gas and thereby eliminate vaporized and entrained salts therefrom.

The effluent gas, now containing vaporized quench liquid, is withdrawn from vessel 33 through line 54 and introduced into a separation and recovery section generally designated as 101. In the separation and recovery section 101, the net chlorinated methane product is recovered and withdrawn through line 102, and unreacted methane and the chlorinated methanes other than the desired chlorinated methane product are recovered and recycled to reactor 33 through line 45. The separation and recovery may be effected in any one of a wide variety of ways known in the art with the specific recovery scheme being dependent upon the chlorinated methane which is recovered as product.

A molten salt is withdrawn from the bottom of reactor 33 through line 61 and lifted by lift gas in line 26 into a separation vessel 62 positioned adjacent the top of reactor 11. In separator 62, the molten salt is separated from the lift gas and introduced throgh line 10 into vessel 11. The lift gas is withdrawn from separator 62 through line 62 and combined with the lift gas in line 35 for introduction into the top quenching section of vessel 11 through line 13.

Reference is now made to FIG. 2 of the drawings which illustrates a representative embodiment for the recovery of net chlorinated methane product of methylene chloride and chloroform, with methyl chloride and carbon tetrachloride being used in an amount which eliminates net production thereof. In this embodiment, the net product includes an amount of chloroform which requires recycle of some methylene chloride, (the amount recycled is not sufficient to eliminate net production therof) but it is to be understood that, in some cases, methylene chloride and chloroform may be produced as net product without recycle of methylene chloride. It is also to be understood that methylene chloride could be used in an amount to eliminate net production thereof in which case chloroform is the only net product.

Referring now to FIG. 2, the reaction effluent in line 54 is cooled in condenser 110, primarily to condense a portion of the water therefrom (the condensed water would also contain hydrogen chloride, if present), the aforesaid cooling also resulting in the condensation of chlorinated hydrocarbons, including the chlorinated hydrocarbons used as quench liquid. The condensed water and chlorinated hydrocarbons are separated in a separator 111, with a water phase being withdrawn through line 112 and a chlorinated hydrocarbon phase being withdrawn through line 113. A portion of the chlorinated hydrocarbons in line 113 is recycled through line 53 as quench liquid for reactor 33. Alternatively, all of such chlorinated hydrocarbons, if required, may be recycled as quench liquid. The water phase in line 112, is stripped of entrained and dissolved chlorinated hydrocarbon in a stripping column (not shown) and the recovered chlorinated hydrocarbons (from the stripping column) in line 122a are combined with the chlorinated hydrocarbons in line 113. Depending on the amount of hydrogen chloride present in the water, the water may also be treated to recover hydrogen chloride or a concentrated solution of hydrogen chloride.

The remaining portion of the gaseous effluent in line 114 is optionally passed through an alkali scrubbing zone of a type known in the art, schematically indicated as 115, to remove any remaining hydrogen chloride therefrom.

The gaseous effluent from the alkali scrubbing zone 115, if used, in line 116 is generally passed through a further cooling and separation zone, schematically indicated as 117, to condense further water and chlorinated hydrocarbons therefrom; an acid gas removal zone 118, of a type known in the art, to remove carbon dioxide, and a drier 119, and introduced into a fractional distillation column 121. The chlorinated hydrocarbons in line 113 and chlorinated hydrocarbons separated in zone 117 are combined and dried in drier 120, for introduction into column 121. Alternatively, if required, a portion of the chlorinated hydrocarbons recovered in zone 117, may be recycled as quench liquid to reactor 33. The water separated in zone 117, may be passed to a stripping column to recover any chlorinated hydrocarbons with such recovered chlorinated hydrocarbons also being introduced into column 121.

The column 121 is operated at temperatures and pressures to recover, as overhead, components lighter than methylene chloride; namely methane and methyl chloride. The overhead from column 121 in line 45 is recycled to reactor 33.

The bottoms from column 121 in line 122 is introduced into fractional distillation column 123 operated at temperatures and pressures to recover methylene chloride as overhead. A portion of the methylene chloride overhead in line 124 is recycled to reactor 33, and the remaining portion is recovered as net product.

The bottoms from column 123 in line 125 is introduced into fractional distillation column 126 operated at temperatures and pressures to recover chloroform as overhead. The chloroform overhead is recovered as net product in line 127.

The bottoms from column 126 in line 128 is primarily comprised of carbon tetrachloride and also some dimers, and the bottoms may be introduced into a fractional distillation column 129 operated at temperatures and pressures to recover carbon tetrachloride as overhead. The carbon tetrachloride overhead, in line 131, is recycled to reactor 33.

The bottoms comprised of dimers in line 132 may be introduced into a combustion zone 133 along with an oxygen containing gas in line 134 to effect combustion thereof and thereby recover chlorine values as hydrogen chloride and chlorine. A combustion effluent is withdrawn from zone 133 and introduced into reactor 11 wherein the chlorine and hydrogen chloride are recovered therefrom. The general technique for recovering chlorine values by combustion of chlorinated hydrocarbons is described in U.S. Pat. No. 3,548,016 and U.S. application Ser. No. 95,030 which are hereby incorporated by reference.

The invention is further illustrated by the following examples, but it is to be understood that the scope of the invention is not to be limited thereby.

EXAMPLE I

The following feeds are contacted with a molten mixture comprising 39.4% cupric chloride, 2.6% copper oxychloride, 30% potassium chloride and 28% cuprous chloride at a temperature of 840° F and atmospheric pressure.

| Example | Feed - Mol % | | | |
| --- | --- | --- | --- | --- |
| | $CH_4$ | $Cl_2$ | HCl | $CCl_4$ |
| I | 63.9 | 22.3 | 0 | 13.8 |
| II | 38.6 | 25.7 | 0 | 35.7 |

| Example | Net Product Mol % | | | | |
| --- | --- | --- | --- | --- | --- |
| | $CH_3Cl$ | $CH_2Cl_2$ | $CHCl_3$ | $CCl_4$ | Dimers |
| I | 38 | 24 | 36.0 | 0 | 2 |
| II | 21.8 | 31.5 | 44.0 | 0 | 2.7 |

In accordance with the present invention, the production of carbon tetrachloride is essentially eliminated, and such a result is achieved without limiting per pass methane conversion. Although such a process may result in an increase in the production of dimers, such an increase may be more than compensated by the ability to increase methane conversion and the fact that the chlorine values of such dimers may be recovered by combustion as hereinabove described. Furthermore, the total amount of methane converted to dimers is less than the total amount of methane which would have been converted to carbon tetrachloride and, accordingly, the total amount of methane converted to unwanted product (carbon tetrachloride plus dimers) is decreased.

The process of the present invention is further advantageous in that such a result may be achieved while minimizing production of carbon oxides.

Numerous modifications and variations of the present invention are possible in light of the above teachings and, therefore, within the scope of the appended claims the invention may be practised other than as particularly described.

We claim:

1. A process for producing as net chlorinated methane reaction product a mixture of methylene chloride and chloroform, without essential net production of carbon tetrachloride, comprising:
   (a) contacting in an oxidation reaction zone a molten salt mixture of cuprous and cupric chloride with molecular oxygen to produce copper oxychloride;
   (b) contacting molten salt mixture from step (a) in an oxychlorination reaction zone with fresh feed methane and chlorine to effect oxychlorination of the methane with oxygen requirements for the oxychlorination being provided by the oxychloride of the molten salt mixture, said contacting being effected at a temperature of from about 700° to about 860° F, at a methane conversion from about 25 to 50 mole percent and in the presence of carbon tetrachloride in an amount to provide tetrachloride to methane mole ratio of at least about 0.2:1 to essentially eliminate net production of carbon tetrachloride;
   (c) withdrawing from the oxychlorination reaction zone an effluent containing unreacted methane, methyl chloride, methylene chloride, chloroform and carbon tetrachloride;

(d) recovering as net product, from the effluent, chloroform and at least a portion of the methylene chloride;

(e) recycling to the oxychlorination reaction zone unreacted methane, methyl chloride and any remaining methylene chloride recovered from the effluent; and (f) passing the molten salt mixture from the oxychlorination reaction zone to the oxidation reaction zone.

2. The process of claim 1 wherein said molten salt mixture includes a melting point depressant selected from the group consisting of the alkali metal chlorides and the heavy metal chlorides of Groups I, II, III and IV of the Periodic Table.

3. The process of claim 2 wherein the melting point depressant is potassium chloride.

4. The process of claim 3 wherein the molten salt mixture introduced into the oxychlorination reaction zone comprises from about 20% to about 40%, by weight, potassium chloride, from about 20% to about 55%, by weight, cupric chloride, from about 0.5% to about 4%, by weight, copper oxychloride, with the remainder being cuprous chloride.

5. The process of claim 1 wherein carbon tetrachloride recovered from the effluent is recycled to the oxychlorination reaction zone.

6. The process of claim 5 wherein the effluent withdrawn from the oxychlorination reaction zone includes hydrogen chloride, said hydrogen chloride being separated from the effluent, the effluent free of hydrogen chloride being introduced into a first fractional distillation zone to recover unreacted methane and methyl chloride as overhead which is recycled to the oxychlorination reaction zone, bottoms from the first fractional distillation zone being introduced into a second fractional distillation zone to recover methylene chloride as overhead with at least a portion thereof being recovered as net product and the remaining portion being recycled to the oxychlorination reaction zone; bottoms from the second fractional distillation zone being introduced into a third fractional distillation zone to recover chloroform as overhead as net reaction product; bottoms from the third fractional distillation zone being introduced into a fourth fractional distillation zone to recover carbon tetrachloride as overhead which is recycled to the oxychlorination reaction zone.

7. A process for producing chloroform, without essential net production of carbon tetrachloride, comprising:

(a) contacting in an oxidation reaction zone a molten salt mixture of cuprous and cupric chloride with molecular oxygen to produce copper oxychloride;

(b) contacting molten salt mixture from step (a) in an oxychlorination reaction zone with fresh feed methane and chlorine to effect oxychlorination of the methane with oxygen requirements for the oxychlorination being provided by the oxychloride of the molten salt mixture, said contacting being effected at a temperature of from about 700° to about 850° F, at a methane conversion from about 25 to 50 mole percent and in the presence of carbon tetrachloride in an amount to provide a carbon tetrachloride to methane mole ratio of at least 0.4:1 to essentially eliminate net production of carbon tetrachloride;

(c) withdrawing from the oxychlorination reaction zone an effluent containing unreacted methane, methyl chloride, methylene chloride, chloroform and carbon tetrachloride;

(d) recovering as net product, from the effluent, chloroform;

(e) recycling to the oxychlorination reaction zone unreacted methane, methyl chloride and methylene chloride recovered from the effluent; and (f) passing the molten salt mixture from the oxychlorination reaction zone to the oxidation reaction zone.

* * * * *

UNITED STATES PATENT OFFICE
CERTIFICATE OF CORRECTION

Patent No. 4,107,222    Dated August 15, 1978

Inventor(s) Morgan C. Sze, Herbert Riegel and D. Schindler

It is certified that error appears in the above-identified patent and that said Letters Patent are hereby corrected as shown below:

In the Specification:

Col. 6, line 33, "throgh" should be --through--;

Col. 6, line 35, "62" should be --64--;

In the Claims:

Col. 8, line 61, after "provide" insert --a carbon--;

Col. 10, line 21, "850°" should be --860°--.

Signed and Sealed this

Twenty-fifth Day of March 1980

[SEAL]

Attest:

SIDNEY A. DIAMOND

Attesting Officer    Commissioner of Patents and Trademarks